US00PP12878P2

(12) United States Plant Patent
Zaiger et al.

(10) Patent No.: US PP12,878 P2
(45) Date of Patent: Aug. 27, 2002

(54) PEACH TREE NAMED: 'SWEET CREST'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 190 days.

(21) Appl. No.: 09/835,767

(22) Filed: Apr. 16, 2001

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Anne Marie Grünberg

(57) ABSTRACT

A new and distinct variety of peach tree, (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of features that are desirable in a new variety:

1. Heavy and regular production of fruit.
2. Vigorous and upright growth.
3. Early maturity of large, yellow flesh, clingstone fruit.
4. Fruit with a high degree of attractive red skin color.
5. Fruit with a mild, sweet, sub-acidic flavor with very good eating quality.

1 Drawing Sheet

BACKGROUND OF THE VARIETY

In the field of plant genetics, we conduct an extensive and continuing plant-breeding program including the organization and a sexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peaches and nectarines, which are known to us, and mentioned herein, are 'May Grand' Nectarine (U.S. Plant Pat. No. 2,794), 'Tasty Gold' Nectarine (U.S. Plant Pat. No. 5,623), 'May Crest' Peach (U.S. Plant Pat. No. 4,064), 'Sam Houston' Peach (non-patented) and 'Springcrest' Peach (non-patented).

ORIGIN OF THE VARIETY

The present variety of peach tree (*Prunus persica*) was originated by us in our experimental orchard located near Modesto, Calif., as an open pollinated seedling from a cross between two selected seedlings with field identification numbers 34GA1155 and 36EB346. The maternal parent (34GA1155) originated from a cross between a seedling selection from a 'May Grand' Nectarine (U.S. Plant Pat. No. 2,794) crossed with a peach of unknown parentage. This selection was then crossed with an open pollinated seedling of 'Sam Houston' Peach (non-patented). The paternal parent (36EB346) originated from a first generation cross of 'Tasty Gold' Nectarine (U.S. Plant Pat. No. 5,623) with 'May Crest' Peach (U.S. Plant Pat. No. 4,064). We planted and maintained a large group of these open pollinated seedlings on their own root system, under close observation we recognized the desirable fruit characteristics of the present variety and selected it in 1993 for asexual propagation and commercialization.

ASEXUAL REPRODUCTION OF THE VARIETY

Asexual reproduction of the new and distinct variety of peach tree was by budding to 'Nemaguard' Rootstock, (non-patented), one of the standard rootstock for peach trees in California, as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The distinct variety of peach tree is of large size, vigorous, upright growth and a productive and regular bearer of large size, yellow flesh, clingstone fruit with good storage and shipping qualities. The fruit is further characterized by its attractive red skin color, firm flesh, mild, sweet, sub-acidic flavor and very good eating quality, and in comparison to 'Springcrest' Peach (non-patented), the fruit of the new variety is larger in size, has mild, sweet, sub-acidic flesh instead of acidic flesh, and is 4 to 5 days later in maturity. In comparison to the 'May Crest' Peach (U.S. Plant Pat. No. 4,064), the new variety has greater production of larger, uniform size fruit, the flesh is sub-acidic instead of acidic and is 11 to 12 days later in maturity and in comparison to 'Sam Houston' Peach (non-patented), the present variety is more round in shape, has a firmer flesh and is approximately 6 weeks earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the variety of peach tree, its flowers, foliage and fruit, as based on observations of 7 year old specimens grown on 'Nemaguard' Rootstock (non-patented) near Modesto, Calif., with color terminology (except those in common terms) in accordance with Reinhold Color Atlas by A. Kornerup and J. H. Wanscher.

Tree:

*Size.*—Large. Tree pruned to 10 to 12 feet in height for economical harvesting of fruit.

*Vigor.*—Vigorous. Grows to a height of 6 to 7 feet the first growing season. Pruned to 4 to 5 feet the first dormant season and primary scaffolds are selected.

*Growth.*—Upright, pruned to vase shape for increased sunlight penetration.

*Branching habit.*—Upright. Width of tree increases with heavy production of fruit, crotch angle approximately 40 degrees.

*Fertility.*—Self-fertile.

*Productivity.*—Productive, producing 1½ to several times the number of fruit for desired crop load. Fruit is thinned and spaced to the desired number.

*Bearer.*—Regular, has produced adequate fruit set for 6 consective years. No alternate bearing observed.

*Density.*—Medium dense. Pruning to open the center of the tree by removing branches is desirable for sunlight penetration.

*Hardiness.*—Tree grown in USDA Hardiness Zone 9. Winter chilling requirement of approximately 850 to 950 hours below 45° F. Hardy in all stone fruit growing areas of California.

Trunk:

*Size.*—Large, stocky. Average circumference of 19 inches at 12 inches above ground on a 7 year old tree. Varies with soil type, climatic conditions and cultural practices.

*Surface texture.*—Medium shaggy. As the tree grows older, small areas of bark project outward giving a rough or shaggy surface, increases with age.

*Color.*—Brownish gray to grayish brown (5-F-2) to (5-F-3).

Branches:

*Size.*—Medium to large. Circumference of 9 inches at 38 inches above the ground.

*Surface texture.*—Smooth to medium rough. Roughness increases with age of branch.

*Lenticels.*—Numerous. Average number of 44 in a 4 square inch surface. Size — small. Average length 5/32 inch. Average width 1/16 inch. Size increases as branches become larger. Color varies from light brown to yellowish brown (5-D-8) to (5-E-8).

*Color.*—One year old wood-grayish green to olive brown (30-C-6) to (4-D-8). Mature wood varies from hair brown to brown (5-E-4) to (5-E-5). Varies with age of growth.

Leaves:

*Size.*—Large. Average length 6 inches. Average width 1½ inches.

*Form.*—Lanceolate, apex acuminate, base cuneate.

*Margin.*—Serrate.

*Thickness.*—Medium.

*Surface texture.*—Upper surface relatively smooth, except for small indentations over midrib and pinnate venation, glabrous. Lower surface relatively smooth, slight ridging with midrib and pinnate venation, glabrous.

*Petiole.*—Medium. Average length 13/32 inch. Average width 1/16 inch. Color varies from grayish green to pale green (29-B-4) to (29-B-6). Grooved longitudinally.

*Glands.*—Reniform. Medium in size. Average diameter 3/64 inch. Number varies from 0 to 4. Average number 2. Color — grayish green (29-C-5). Sticky secretion collects dust, which creates darker color.

*Color.*—Upper Surface — green to dark green (29-E-7) to (29-E-8). Lower Surface — grayish green to green (28-D-6) to (28-D-8).

*Venation.*—Pinnately net veined.

Flower buds:

*Size.*—Large. Average length 9/16 inch. Average diameter 3/8 inch three days before full bloom.

*Hardiness.*—Hardy, wtih respect to central California winters.

*Form.*—Plump, free, conic. Becomes elongated just before opening.

*Color.*—Light pink to pink (11-A-3) to (11-A-4).

*Pubescence.*—Pubescent.

Flowers:

*Size.*—Large, showy. Average height 59/64 inch. Average diameter 1 43/64 inches.

*Petals.*—Number — five, alternately arranged to sepals. Elliptic, edges vary from smooth to slightly scalloped. Narrows at point of attachment. Average length 55/64 inches. Average width 43/64 inch. Color varies from light pink to pink (11-A-3) to (11-A-4). Fades to nearly white at petal fall.

*Sepals.*—Number — five, alternately arranged to petals. Triangular, with smooth edges, apex rounded. Average length 3/16 inch. Average width 3/32 inch at point of attachment. Color — upper surface varies from yellowish green (29-B-6) near the outer area to brownish red (11-D-5) near point of attachment, glabrous. Color lower surface — brownish red to brownish violet (11-D-5) to (11-D-7), pubescent. Colors fade with age of flowers.

*Stamens.*—Number of stamens varies from 38 to 40 per flower. Average number 39. Average length 9/16 inch. Filament color — white (1-A-1), turning pale pink with age. Anther color — red to bluish red (12-A-7) to (12-A-8).

*Pollen.*—Present, self-fertile. Color — light yellow to yellow (3-A-4) to (3-A-6).

*Pistil.*—Usually one. Pubescent. Average length 3/4 inch. Color — yellowish white to pastel yellow (1-A-2) to (1-A-3). Stigma approximately the same height as anthers.

*Pedicel.*—Average length. — 5/32 inch. Average width. — 5/64 inch. Color — grayish yellow (3-B-5).

*Fragrance.*—Wanting.

*Blooming period.*—Date of First Bloom Feb. 24, 2000. Date of Petal Fall Mar. 3, 2000. Varies slightly with climatic conditions.

*Color.*—Light pink to pink (11-A-3) to (11-A-4).

Fruit:

*Maturity when described.*—Mature, firm.

*Date of first picking.*—May 25, 2000.

*Date of last picking.*—May 31, 2000. Varies slightly with climatic conditions.

*Size.*—Average diameter axially 2⅝ inches to 2¾ inches. Average transversely in suture plane 2½ inches to 2¾ inches. Average weight 195.3 grams. Average weight varies slightly with fertility of the soil, amount of thinning and climatic conditions.

*Form.*—Globose to slightly elongated.

*Suture.*—Shallow, extends from base to apex.

*Ventral surface.*—Usually rounded, some fruit slightly lipped.

*Apex.*—Usually rounded, some fruit with very slight pistil point.

*Base.*—Retuse.

*Cavity.*—Slightly elongated in suture plane. Average depth ½ inch. Average breadth ⅝ inch.

Stem:

*Size.*—Average length ½ inch. Average diameter 5/32 inch. Enlarged at point of fruit attachment.

*Color.*—Grayish yellow to olive green (3-C-6) to (3-D-6).

Flesh:

*Ripens.*—Evenly to slightly earlier at the apex.

*Texture.*—Firm, meaty.

*Fibers.*—Few, small and tender.

*Aroma.*—Slight.

*Amydgalin.*—Undetected.

*Eating quality.*—Very good.

*Flavor.*—Very good, mild, sweet, sub-acid.

*Juice.*—Moderate, mild, sub-acid, sweet, enhances flavor.

*Brix.*—Average 10.4°. Varies slightly with amount of fruit per tree and climatic conditions.

*Color.*—Light yellow to maize yellow (4-A-4) to (4-A-6), developing shell pink to pastel red in the flesh after the fruit matures (8-A-3) to (8-A-4). Pit cavity — butter yellow to amber yellow (4-A-5) to (4-B-5). Slight bleeding of pale red to geranium red (11-A-3) to (11-A-7) in small areas near apex on some fruit.

Skin:

*Thickness.*—Medium, smooth, without roughness or reticulation.

*Texture.*—Medium, tenacious to the flesh.

*Tendency to crack.*—None.

*Color.*—Light yellow to yellow ground color (3-A-5) to (3-A-7). Nearly overspread with Turkish red to cardinal red (10-C-8) to (10-D-8).

*Astringency.*—None.

*Pubescence.*—Pubescent, moderate amount, short in length.

Stone:

*Type.*—Clingstone.

*Size.*—Large. Average length 1⅜ inch. Average width 1 inch. Average thickness ¾ inch.

*Form.*—Varies from oval to ovoid.

*Base.*—Usually straight, varies from straight to rounded.

*Apex.*—Acuminate, short in length.

*Surface.*—*Irregularly furrowed toward the apex, pitted toward the base. Pit cavities vary from round to elongated. One large groove on each side of suture. Ridges are relatively wide and nearly smooth.*

*Sides.*—Equal to unequal. Some stones have one side slightly larger, extending further from the suture plane.

*Tendency to split.*—None.

*Color.*—Golden brown to light brown when dry (5-D-7) to (6-D-8).

Kernel:

*Form.*—Oval.

*Taste.*—Bitter.

*Viability.*—Viable.

*Size.*—Average length 49/64 inch, average width 29/64 inch.

*Skin color.*—Tan to light orange (5-B-4) to (5-B-5), when dry.

Use: Dessert.

*Market.*—Local and long distance.

Keeping quality: Good, holds well on tree after maturity and for 2 weeks in cold storage at 38° to 42° F. without internal breakdown.

Shipping quality: Good, picking and packing of fruit gave minimal bruising or scarring of flesh or skin.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous upright growth; being a productive and regular bearer of large size, yellow flesh, clingstone fruit that has a mild, sweet, sub-acidic flavor with very good eating quality; the fruit is further characterized by its attractive red skin color, firm flesh, good shipping and storage qualities and, in compariosn to the fruit of the 'Springcrest' Peach (non-patented), the fruit of the new variety is larger in size, mild, sweet, sub-acidic in flavor instead of acidic and is approximately 4 to 5 days later in maturity.

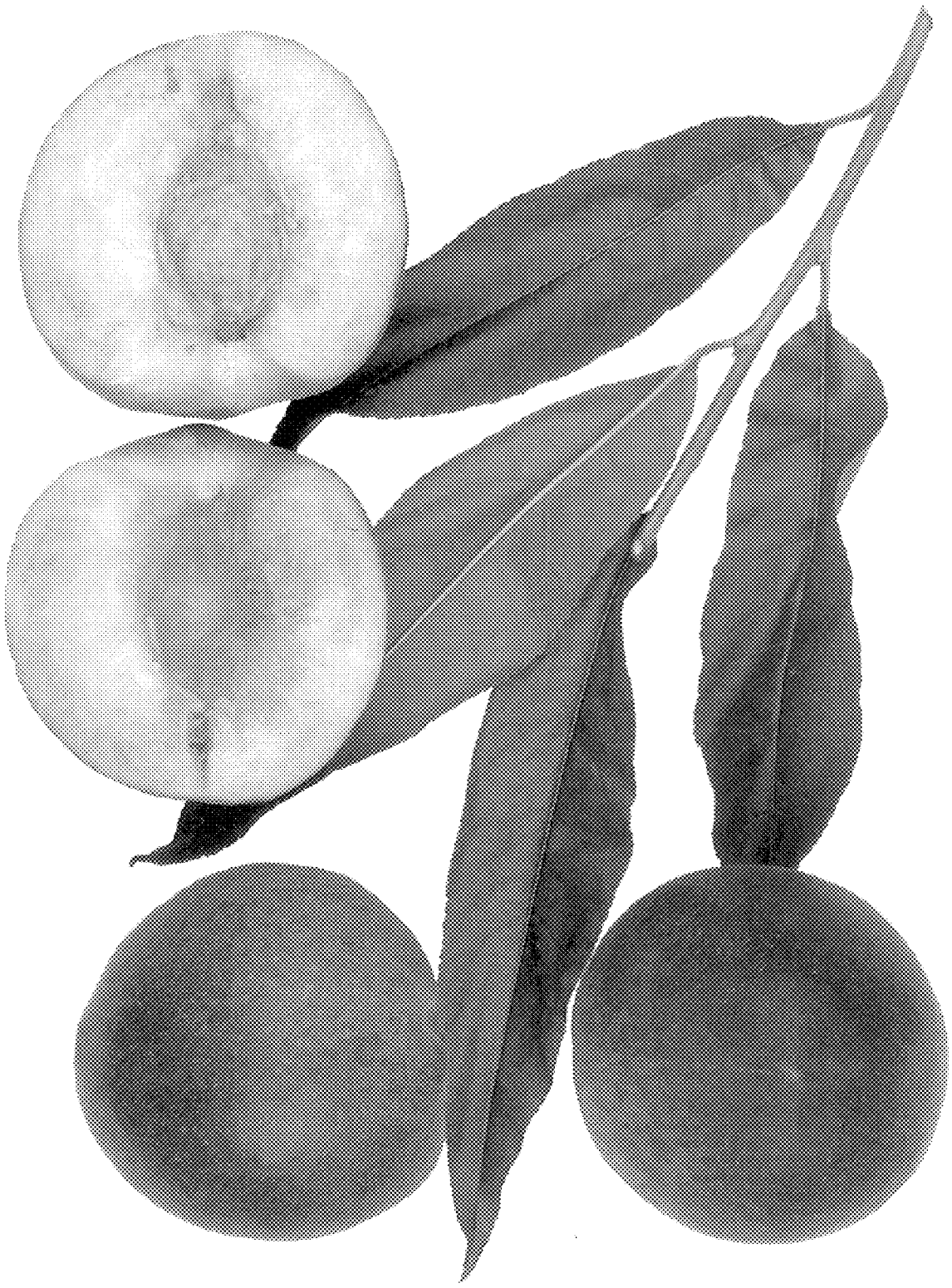

* * * * *